United States Patent
Remington et al.

(10) Patent No.: US 9,526,525 B2
(45) Date of Patent: Dec. 27, 2016

(54) PERCUTANEOUS SYSTEM FOR DYNAMIC SPINAL STABILIZATION

(75) Inventors: Benjamin J. Remington, Modesto, CA (US); Daniel R. Baker, Seattle, WA (US); Stuart B. Mitchell, Lake Forest Park, WA (US); Jeffrey R. Mirisola, Bothell, WA (US); John I. Green, Burke, VA (US)

(73) Assignee: Neuropro Technologies, Inc., Modesto, CA (US)

( * ) Notice: Subject to any disclaimer, the term of this patent is extended or adjusted under 35 U.S.C. 154(b) by 1622 days.

(21) Appl. No.: 11/771,770

(22) Filed: Jun. 29, 2007

(65) Prior Publication Data
US 2008/0051787 A1 Feb. 28, 2008

Related U.S. Application Data

(60) Provisional application No. 60/823,246, filed on Aug. 22, 2006.

(51) Int. Cl.
*A61B 17/70* (2006.01)
*A61B 17/88* (2006.01)

(52) U.S. Cl.
CPC ....... *A61B 17/7031* (2013.01); *A61B 17/7005* (2013.01); *A61B 17/7032* (2013.01); *A61B 17/7083* (2013.01); *A61B 17/8869* (2013.01); *A61B 17/70* (2013.01); *A61B 17/7002* (2013.01); *A61B 17/708* (2013.01);
(Continued)

(58) Field of Classification Search
CPC ........................... A61B 17/70–17/7046; A61B 17/7032–17/7034
USPC ................................ 606/250–260, 264–272
See application file for complete search history.

(56) References Cited

U.S. PATENT DOCUMENTS

| | | | |
|---|---|---|---|
| 4,309,777 A | 1/1982 | Patil | |
| 4,863,476 A | 9/1989 | Sheppard | |
| 4,961,740 A | 10/1990 | Ray et al. | |

(Continued)

FOREIGN PATENT DOCUMENTS

| | | |
|---|---|---|
| EP | 0727188 B1 | 11/1998 |
| EP | 0669109 B1 | 5/1999 |

(Continued)

OTHER PUBLICATIONS

"Dynesys Dynamic Stabilization System", Zimmer, pp. 1-4, last updated Jul. 21, 2005.*
(Continued)

*Primary Examiner* — Thomas J Sweet
*Assistant Examiner* — Rebecca Preston
(74) *Attorney, Agent, or Firm* — Haverstock & Owens LLP

(57) ABSTRACT

A minimally invasive, percutaneous system that allows for dynamic stabilization of the spine is provided, together with methods of using the system. The system comprises a first bone anchoring member that is anchored in a first vertebra, and a second bone anchoring member that is anchored in a second, adjacent, vertebra. The first and second bone anchoring members include a first head portion and second head portion, respectively, that are designed to hold first and second ends of a flexible, elongated member, or cord. In certain embodiments, the cord is provided with a stiffened, relatively inflexible, end portion that is fixedly attached to the cord and that facilitates threading of the cord through the first and second head portions.

14 Claims, 9 Drawing Sheets

(52) U.S. Cl.
CPC ....... *A61B 17/7019* (2013.01); *A61B 17/7023* (2013.01); *A61B 17/7026* (2013.01); *A61B 17/7074* (2013.01)

(56) References Cited

U.S. PATENT DOCUMENTS

| | | | |
|---|---|---|---|
| 5,015,247 | A | 5/1991 | Michelson |
| 5,059,193 | A | 10/1991 | Kuslich |
| 5,084,048 | A | 1/1992 | Jacob et al. |
| 5,123,926 | A | 6/1992 | Pisharodi |
| 5,171,278 | A | 12/1992 | Pisharodi |
| 5,443,514 | A | 8/1995 | Steffee |
| 5,458,642 | A | 10/1995 | Beer et al. |
| 5,522,899 | A | 6/1996 | Michelson |
| 5,653,763 | A | 8/1997 | Errico et al. |
| 5,658,335 | A | 8/1997 | Allen |
| 5,665,122 | A | 9/1997 | Kambin |
| 5,693,100 | A | 12/1997 | Pisharodi |
| 5,702,391 | A | 12/1997 | Lin |
| 5,716,415 | A | 2/1998 | Steffee |
| 5,782,832 | A | 7/1998 | Larsen et al. |
| 5,800,547 | A | 9/1998 | Schafer et al. |
| 5,800,550 | A | 9/1998 | Sertich |
| 5,827,328 | A | 10/1998 | Buttermann |
| 5,865,848 | A | 2/1999 | Baker |
| 5,885,287 | A | 3/1999 | Bagby |
| 5,928,284 | A | 7/1999 | Mehdizadeh |
| 5,980,522 | A | 11/1999 | Koros et al. |
| 6,045,579 | A | 4/2000 | Hochshuler et al. |
| 6,080,158 | A | 6/2000 | Lin |
| 6,080,193 | A | 6/2000 | Hochshuler et al. |
| 6,102,949 | A | 8/2000 | Biedermann et al. |
| 6,102,950 | A | 8/2000 | Vaccaro |
| 6,117,174 | A | 9/2000 | Nolan |
| 6,129,763 | A | 10/2000 | Chauvin et al. |
| 6,156,067 | A | 12/2000 | Bryan et al. |
| 6,159,244 | A | 12/2000 | Suddaby |
| 6,174,334 | B1 | 1/2001 | Suddaby |
| 6,176,881 | B1 | 1/2001 | Schar et al. |
| 6,176,882 | B1 | 1/2001 | Biedermann et al. |
| 6,179,873 | B1 | 1/2001 | Zientek |
| 6,183,517 | B1 | 2/2001 | Suddaby |
| 6,190,414 | B1 | 2/2001 | Young et al. |
| 6,231,609 | B1 | 5/2001 | Mehdizadeh |
| 6,342,074 | B1 | 1/2002 | Simpson |
| 6,371,968 | B1 | 4/2002 | Kogasaka et al. |
| 6,371,987 | B1 | 4/2002 | Weiland et al. |
| 6,375,655 | B1 | 4/2002 | Zdeblick et al. |
| 6,375,683 | B1 | 4/2002 | Crozet et al. |
| 6,409,766 | B1 | 6/2002 | Brett |
| 6,419,705 | B1 | 7/2002 | Erickson |
| 6,436,140 | B1 | 8/2002 | Liu et al. |
| 6,443,989 | B1 | 9/2002 | Jackson |
| 6,454,806 | B1 | 9/2002 | Cohen et al. |
| 6,454,807 | B1 | 9/2002 | Jackson |
| 6,464,727 | B1 | 10/2002 | Sharkey et al. |
| 6,488,710 | B2 | 12/2002 | Besselink |
| 6,491,695 | B1 | 12/2002 | Roggenbuck |
| 6,527,803 | B1 | 3/2003 | Crozet et al. |
| 6,530,929 | B1 | 3/2003 | Justis et al. |
| 6,562,041 | B1 | 5/2003 | Yonemura et al. |
| 6,572,619 | B2 | 6/2003 | Santilli |
| 6,572,653 | B1 | 6/2003 | Simonson |
| 6,576,016 | B1 | 6/2003 | Hochshuler et al. |
| 6,582,431 | B1 | 6/2003 | Ray |
| 6,582,467 | B1 | 6/2003 | Teitelbaum et al. |
| 6,595,995 | B2 | 7/2003 | Zdeblick et al. |
| 6,613,091 | B1 | 9/2003 | Zdeblick et al. |
| 6,616,667 | B1 | 9/2003 | Steiger et al. |
| 6,645,249 | B2 | 11/2003 | Ralph et al. |
| 6,652,584 | B2 | 11/2003 | Michelson |
| 6,666,888 | B1 | 12/2003 | Jackson |
| 6,685,742 | B1 | 2/2004 | Jackson |
| 6,706,070 | B1 | 3/2004 | Wagner et al. |
| 6,709,458 | B2 | 3/2004 | Michelson |
| 6,723,126 | B1 | 4/2004 | Berry |
| 6,723,128 | B2 | 4/2004 | Uk |
| 6,746,454 | B2 | 6/2004 | Winterbottom et al. |
| 6,767,367 | B1 | 7/2004 | Michelson |
| 6,770,095 | B2 | 8/2004 | Grinberg et al. |
| 6,770,096 | B2 | 8/2004 | Bolger et al. |
| 6,783,527 | B2 | 8/2004 | Drewry et al. |
| 6,808,537 | B2 | 10/2004 | Michelson |
| 6,821,298 | B1 | 11/2004 | Jackson |
| 6,830,589 | B2 | 12/2004 | Erickson |
| 6,835,206 | B2 | 12/2004 | Jackson |
| 6,902,568 | B2 | 6/2005 | Serhan |
| 6,923,830 | B2 | 8/2005 | Michelson |
| 6,962,606 | B2 | 11/2005 | Michelson |
| 6,979,353 | B2 | 12/2005 | Bresina |
| 6,989,011 | B2 | 1/2006 | Paul et al. |
| 7,008,453 | B1 | 3/2006 | Michelson |
| 7,011,660 | B2 | 3/2006 | Sherman et al. |
| 7,018,415 | B1 | 3/2006 | McKay |
| 7,041,309 | B2 | 5/2006 | Remington et al. |
| 7,048,763 | B2 | 5/2006 | Ralph et al. |
| 7,073,415 | B2 | 7/2006 | Casutt et al. |
| 7,094,257 | B2 | 8/2006 | Mujwid et al. |
| 7,108,862 | B2 | 9/2006 | Remington et al. |
| 7,118,598 | B2 | 10/2006 | Michelson |
| 7,125,410 | B2 | 10/2006 | Freudiger |
| 7,128,760 | B2 | 10/2006 | Michelson |
| 7,166,130 | B2 | 1/2007 | Ferree |
| 7,211,112 | B2 | 5/2007 | Baynham et al. |
| 7,217,291 | B2 | 5/2007 | Zucherman et al. |
| 7,217,293 | B2 | 5/2007 | Branch, Jr. |
| 7,220,280 | B2 | 5/2007 | Kast et al. |
| 7,235,103 | B2 | 6/2007 | Rivin |
| 7,238,186 | B2 | 7/2007 | Zdeblick et al. |
| 7,331,994 | B2 | 2/2008 | Gordon et al. |
| 7,331,996 | B2 | 2/2008 | Soto et al. |
| 7,431,735 | B2 | 10/2008 | Liu et al. |
| 7,445,636 | B2 | 11/2008 | Michelson |
| 7,479,160 | B2 | 1/2009 | Branch et al. |
| 7,500,992 | B2 | 3/2009 | Li |
| 7,537,612 | B2 | 5/2009 | Kunzler |
| 7,578,849 | B2 | 8/2009 | Trieu |
| 7,584,682 | B2 | 9/2009 | Hsiao |
| 7,608,107 | B2 | 10/2009 | Michelson |
| 7,621,956 | B2 | 11/2009 | Paul et al. |
| 7,674,296 | B2 | 3/2010 | Rhonda et al. |
| 7,678,148 | B2 | 3/2010 | Peterman |
| 7,682,376 | B2 | 3/2010 | Trieu |
| 7,691,147 | B2 | 4/2010 | Gutlin et al. |
| 7,703,727 | B2 | 4/2010 | Seiness |
| 7,727,280 | B2 | 6/2010 | McLuen |
| 7,749,252 | B2 | 7/2010 | Zucherman et al. |
| 7,753,958 | B2 | 7/2010 | Gordon et al. |
| 7,758,617 | B2 | 7/2010 | Lott et al. |
| 7,794,501 | B2 | 9/2010 | Edie et al. |
| 7,799,081 | B2 | 9/2010 | McKinley |
| D626,233 | S | 10/2010 | Cipoletti et al. |
| 7,811,287 | B2 | 10/2010 | Errico et al. |
| 7,811,327 | B2 | 10/2010 | Hansell et al. |
| 7,828,849 | B2 | 11/2010 | Lim |
| 7,837,688 | B2 | 11/2010 | Boyer, II et al. |
| 7,837,734 | B2 | 11/2010 | Zucherman et al. |
| 7,850,733 | B2 | 12/2010 | Baynham et al. |
| 7,931,688 | B2 | 4/2011 | Landry et al. |
| 7,932,825 | B2 | 4/2011 | Berger |
| RE42,480 | E | 6/2011 | Bryan et al. |
| 7,985,231 | B2 | 7/2011 | Sankaran |
| 8,002,834 | B2 | 8/2011 | de Villiers et al. |
| 8,062,375 | B2 | 11/2011 | Gierum et al. |
| 8,070,813 | B2 | 12/2011 | Grotz et al. |
| 8,105,382 | B2 | 1/2012 | Olmos et al. |
| 8,110,004 | B2 | 2/2012 | Valdevit et al. |
| 8,187,332 | B2 | 5/2012 | McLuen |
| 8,221,502 | B2 | 7/2012 | Branch, Jr. |
| 8,262,666 | B2 | 9/2012 | Baynham et al. |
| 8,262,736 | B2 | 9/2012 | Michelson |
| 8,273,129 | B2 | 9/2012 | Baynham et al. |
| 8,282,683 | B2 | 10/2012 | McLaughlin et al. |
| 8,292,963 | B2 | 10/2012 | Miller et al. |

(56) References Cited

U.S. PATENT DOCUMENTS

| | | |
|---|---|---|
| 8,303,601 B2 | 11/2012 | Bandeira et al. |
| 8,303,658 B2 | 11/2012 | Peterman |
| 8,308,801 B2 | 11/2012 | Halverson et al. |
| 8,308,804 B2 | 11/2012 | Kruegar |
| 8,317,025 B1 | 11/2012 | Kolozs et al. |
| 8,328,962 B2 | 12/2012 | Schussler |
| 8,337,562 B2 | 12/2012 | Landry et al. |
| 8,343,222 B2 | 1/2013 | Cope |
| 8,361,152 B2 | 1/2013 | McCormack et al. |
| 8,366,777 B2 | 2/2013 | Matthis et al. |
| 8,403,990 B2 | 3/2013 | Dryer et al. |
| 8,444,696 B2 | 5/2013 | Michelson |
| 8,444,697 B1 | 5/2013 | Butler et al. |
| 8,585,763 B2 | 11/2013 | Olevsky et al. |
| 8,591,587 B2 | 11/2013 | Refai et al. |
| 8,597,360 B2 | 12/2013 | McLuen et al. |
| 8,690,886 B2 | 4/2014 | Fedorov et al. |
| 8,740,980 B2 | 6/2014 | Merves |
| 8,894,710 B2 | 11/2014 | Simpson et al. |
| 2002/0128716 A1 | 9/2002 | Cohen et al. |
| 2002/0165613 A1 | 11/2002 | Lin et al. |
| 2004/0024461 A1 | 2/2004 | Ferree |
| 2004/0039448 A1 | 2/2004 | Pisharodi |
| 2004/0049190 A1 | 3/2004 | Biedermann et al. |
| 2004/0087947 A1 | 5/2004 | Lim et al. |
| 2004/0106998 A1 | 6/2004 | Ferree |
| 2004/0127993 A1 | 7/2004 | Kast et al. |
| 2004/0138750 A1 | 7/2004 | Michell |
| 2004/0181285 A1 | 9/2004 | Simonson |
| 2004/0204762 A1 | 10/2004 | Ralph et al. |
| 2004/0230309 A1 | 11/2004 | DiMauro et al. |
| 2004/0243238 A1 | 12/2004 | Arnin et al. |
| 2005/0015149 A1 | 1/2005 | Michelson |
| 2005/0038515 A1 | 2/2005 | Kunzler |
| 2005/0065516 A1 | 3/2005 | Jahng |
| 2005/0065517 A1 | 3/2005 | Chin |
| 2005/0065610 A1 | 3/2005 | Pisharodi |
| 2005/0107878 A1 | 5/2005 | Conchy |
| 2005/0131408 A1 | 6/2005 | Sicvol et al. |
| 2005/0143737 A1 | 6/2005 | Pafford et al. |
| 2005/0149020 A1* | 7/2005 | Jahng ............................ 606/61 |
| 2005/0278036 A1 | 12/2005 | Leonard et al. |
| 2005/0283236 A1 | 12/2005 | Razian |
| 2006/0052872 A1 | 3/2006 | Studer et al. |
| 2006/0069436 A1 | 3/2006 | Sutton et al. |
| 2006/0095136 A1 | 5/2006 | McLuen |
| 2006/0111712 A1 | 5/2006 | Jackson |
| 2006/0111713 A1 | 5/2006 | Jackson |
| 2006/0111715 A1 | 5/2006 | Jackson |
| 2006/0116769 A1 | 6/2006 | Marnay et al. |
| 2006/0122701 A1 | 6/2006 | Kiester |
| 2006/0129244 A1 | 6/2006 | Ensign |
| 2006/0149381 A1 | 7/2006 | Kim |
| 2006/0190084 A1 | 8/2006 | Doubler et al. |
| 2006/0200243 A1 | 9/2006 | Rothman et al. |
| 2006/0241643 A1 | 10/2006 | Lim et al. |
| 2006/0241764 A1 | 10/2006 | Michelson |
| 2006/0241766 A1 | 10/2006 | Felton et al. |
| 2006/0241767 A1 | 10/2006 | Doty |
| 2006/0241770 A1 | 10/2006 | Rhoda et al. |
| 2006/0241774 A1 | 10/2006 | Attali et al. |
| 2006/0276899 A1 | 12/2006 | Zipnick et al. |
| 2006/0293752 A1 | 12/2006 | Moumene et al. |
| 2006/0293753 A1 | 12/2006 | Thramann |
| 2007/0050030 A1 | 3/2007 | Kim |
| 2007/0067038 A1 | 3/2007 | Studer et al. |
| 2007/0093897 A1 | 4/2007 | Gerbee et al. |
| 2007/0093901 A1 | 4/2007 | Grotz et al. |
| 2007/0191954 A1 | 8/2007 | Hansell et al. |
| 2007/0233254 A1 | 10/2007 | Grotz et al. |
| 2007/0255407 A1 | 11/2007 | Castleman et al. |
| 2007/0255413 A1 | 11/2007 | Edie et al. |
| 2007/0255415 A1 | 11/2007 | Edie et al. |
| 2007/0270954 A1 | 11/2007 | Wu |
| 2007/0270968 A1 | 11/2007 | Baynham et al. |
| 2007/0288011 A1* | 12/2007 | Logan ............................ 606/61 |
| 2008/0009880 A1 | 1/2008 | Warnick et al. |
| 2008/0015701 A1 | 1/2008 | Garcia et al. |
| 2008/0021559 A1 | 1/2008 | Thramann |
| 2008/0046083 A1 | 2/2008 | Hewko |
| 2008/0051902 A1 | 2/2008 | Dwyer |
| 2008/0077153 A1 | 3/2008 | Pemsteiner et al. |
| 2008/0125778 A1 | 5/2008 | Li |
| 2008/0132949 A1 | 6/2008 | Aferzon et al. |
| 2008/0140207 A1 | 6/2008 | Olmos et al. |
| 2008/0147193 A1 | 6/2008 | Matthis et al. |
| 2008/0154381 A1 | 6/2008 | Parrish |
| 2008/0208264 A1 | 8/2008 | Lazarof |
| 2008/0269905 A1 | 10/2008 | Link |
| 2008/0288076 A1 | 11/2008 | Soo et al. |
| 2009/0099601 A1 | 4/2009 | Aferzon et al. |
| 2009/0164020 A1 | 6/2009 | Janowski et al. |
| 2009/0198241 A1 | 8/2009 | Phan |
| 2009/0198245 A1 | 8/2009 | Phan |
| 2009/0198338 A1 | 8/2009 | Phan |
| 2009/0210061 A1 | 8/2009 | Sledge |
| 2009/0222100 A1 | 9/2009 | Cipoletti et al. |
| 2009/0222101 A1 | 9/2009 | de Villiers et al. |
| 2009/0292361 A1 | 11/2009 | Lopez |
| 2009/0299478 A1 | 12/2009 | Carls et al. |
| 2010/0023057 A1 | 1/2010 | Aeschlimann et al. |
| 2010/0057204 A1 | 3/2010 | Kadaba et al. |
| 2010/0145456 A1 | 6/2010 | Simpson et al. |
| 2010/0204795 A1 | 8/2010 | Greenhalgh |
| 2010/0211119 A1 | 8/2010 | Refai et al. |
| 2010/0211176 A1 | 8/2010 | Greenhalgh |
| 2010/0222884 A1 | 9/2010 | Greenhalgh |
| 2010/0234956 A1 | 9/2010 | Attia et al. |
| 2010/0241231 A1 | 9/2010 | Marino et al. |
| 2010/0256768 A1 | 10/2010 | Lim et al. |
| 2010/0262247 A1 | 10/2010 | Arnin |
| 2010/0280622 A1 | 11/2010 | McKinley |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0298939 A1 | 11/2010 | Delfosse et al. |
| 2010/0324606 A1 | 12/2010 | Moskowitz et al. |
| 2011/0015747 A1 | 1/2011 | McManus et al. |
| 2011/0035011 A1 | 2/2011 | Cain |
| 2011/0054621 A1 | 3/2011 | Lim |
| 2011/0077738 A1 | 3/2011 | Ciupik et al. |
| 2011/0087329 A1 | 4/2011 | Poulos |
| 2011/0112587 A1 | 5/2011 | Patel et al. |
| 2011/0130835 A1 | 6/2011 | Ashley et al. |
| 2011/0130838 A1 | 6/2011 | Lopez |
| 2011/0138948 A1 | 6/2011 | Jimenez et al. |
| 2011/0160861 A1 | 6/2011 | Jimenez et al. |
| 2011/0172716 A1 | 7/2011 | Glerum |
| 2011/0172774 A1 | 7/2011 | Varela |
| 2011/0213465 A1 | 9/2011 | Landry et al. |
| 2011/0218627 A1 | 9/2011 | Rampersaud et al. |
| 2011/0230970 A1 | 9/2011 | Lynn et al. |
| 2011/0238184 A1 | 9/2011 | Zdeblick et al. |
| 2011/0282453 A1 | 11/2011 | Greenhalgh et al. |
| 2011/0301712 A1 | 12/2011 | Palmatier et al. |
| 2011/0319997 A1 | 12/2011 | Glerum et al. |
| 2012/0035729 A1 | 2/2012 | Glerum |
| 2012/0058451 A1 | 3/2012 | Lazarof |
| 2012/0059470 A1 | 3/2012 | Weiman |
| 2012/0059472 A1 | 3/2012 | Weiman |
| 2012/0059473 A1 | 3/2012 | Weiman |
| 2012/0059474 A1 | 3/2012 | Weiman |
| 2012/0059475 A1 | 3/2012 | Weiman |
| 2012/0059481 A1 | 3/2012 | Abernathie et al. |
| 2012/0064487 A1 | 3/2012 | Lazarof |
| 2012/0064488 A1 | 3/2012 | Lazarof |
| 2012/0071979 A1 | 3/2012 | Zipnick |
| 2012/0089228 A1 | 4/2012 | Poulos |
| 2012/0130494 A1 | 5/2012 | DeLurio et al. |
| 2012/0136448 A1 | 5/2012 | Seifert et al. |
| 2012/0143194 A1 | 6/2012 | Seifert et al. |
| 2012/0143201 A1 | 6/2012 | Seifert et al. |
| 2012/0150304 A1 | 6/2012 | Glerum et al. |
| 2012/0150305 A1 | 6/2012 | Glerum et al. |

(56) References Cited

U.S. PATENT DOCUMENTS

| | | |
|---|---|---|
| 2012/0158071 A1 | 6/2012 | Jimenez et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0191194 A1 | 7/2012 | Oimos et al. |
| 2012/0197404 A1 | 8/2012 | Brun et al. |
| 2012/0203347 A1 | 8/2012 | Glerum et al. |
| 2012/0209384 A1 | 8/2012 | Arnold et al. |
| 2012/0226357 A1 | 9/2012 | Varela |
| 2012/0232601 A1 | 9/2012 | Chabansky et al. |
| 2012/0245691 A1 | 9/2012 | Reimeis |
| 2012/0271422 A1 | 10/2012 | Miller et al. |
| 2012/0277875 A1 | 11/2012 | Arnin |
| 2012/0290090 A1 | 11/2012 | Glerum et al. |
| 2012/0303124 A1 | 11/2012 | McLuen et al. |
| 2012/0310350 A1 | 12/2012 | Farris et al. |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0006364 A1 | 1/2013 | McCormack et al. |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0023993 A1 | 1/2013 | Weiman |
| 2013/0023994 A1 | 1/2013 | Glerum |
| 2013/0030534 A1 | 1/2013 | DeLurio et al. |
| 2013/0035724 A1 | 2/2013 | Fitzpatrick |
| 2013/0035763 A1 | 2/2013 | Krueger |
| 2013/0053962 A1 | 2/2013 | Moskowitz et al. |
| 2013/0085572 A1 | 4/2013 | Glerum et al. |
| 2013/0103153 A1 | 4/2013 | Blackwell et al. |
| 2013/0103156 A1 | 4/2013 | Packer et al. |
| 2013/0110248 A1 | 5/2013 | Zipnick |
| 2013/0158663 A1 | 6/2013 | Miller et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0197642 A1 | 8/2013 | Ernst |
| 2013/0204371 A1 | 8/2013 | McLuen et al. |
| 2013/0211525 A1 | 8/2013 | McLuen et al. |
| 2013/0253650 A1 | 9/2013 | Ashley et al. |
| 2013/0274883 A1 | 10/2013 | McLuen et al. |
| 2013/0310938 A1 | 11/2013 | Soumac et al. |
| 2014/0088708 A1 | 3/2014 | McLaughlin et al. |
| 2014/0156006 A1 | 6/2014 | Bannigan et al. |
| 2014/0236296 A1 | 8/2014 | Wagner et al. |
| 2014/0249629 A1 | 9/2014 | Moskowitz et al. |
| 2014/0257485 A1 | 9/2014 | Matthis et al. |
| 2014/0277470 A1 | 9/2014 | Baynham |
| 2014/0277500 A1 | 9/2014 | Logan et al. |
| 2014/0277509 A1 | 9/2014 | Robinson et al. |
| 2014/0288652 A1 | 9/2014 | Boehm et al. |
| 2014/0316522 A1 | 10/2014 | Weiman et al. |
| 2014/0343677 A1 | 11/2014 | Davis et al. |
| 2014/0343678 A1 | 11/2014 | Suddaby et al. |
| 2015/0094815 A1 | 4/2015 | Drori et al. |

FOREIGN PATENT DOCUMENTS

| | | |
|---|---|---|
| FR | 2777449 A1 | 10/1999 |
| WO | 2006134262 A1 | 12/2006 |
| WO | 2008086276 A2 | 7/2008 |
| WO | 2013023096 A1 | 2/2013 |

OTHER PUBLICATIONS

Mueller, Wolfgang "Dynamic Re-Stabilization of Spinal Segments," Sulzer Medica Journal, Ed. Feb. 1998, Sulzer Orthopedics, Ltd., Baar Switzerland.

DePuySpine Products, "Viper System," http://www.depuyspine.com/products/mis/viper.asp, Aug. 15, 2006, DePuy Spine, Inc., California.

Search Report from European Application No. EP13797446, dated Jan. 26, 2016.

* cited by examiner

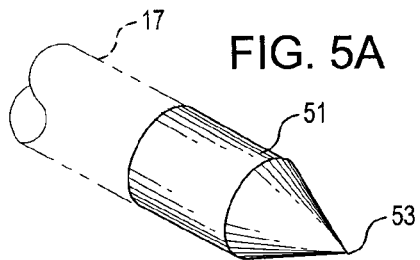
FIG. 5A
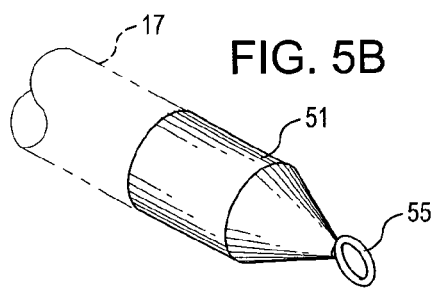
FIG. 5B
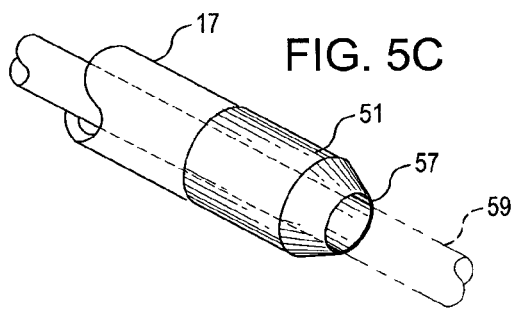
FIG. 5C
FIG. 5D
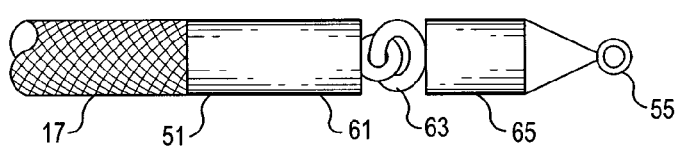
FIG. 5E
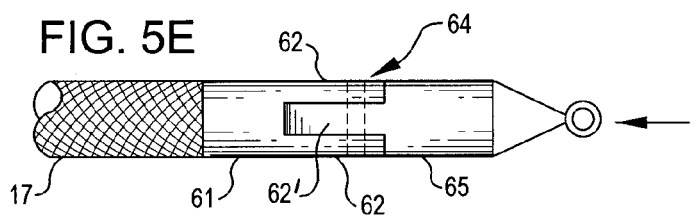
FIG. 5F
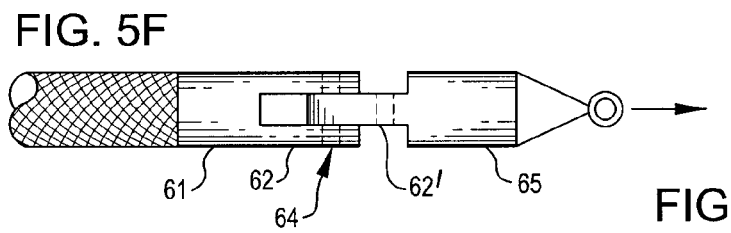
FIG. 5H
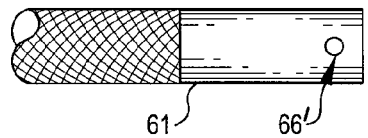
FIG. 5G
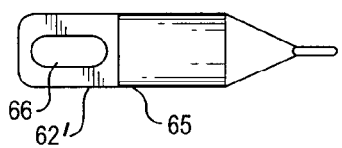
FIG. 5I
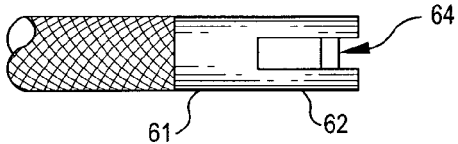

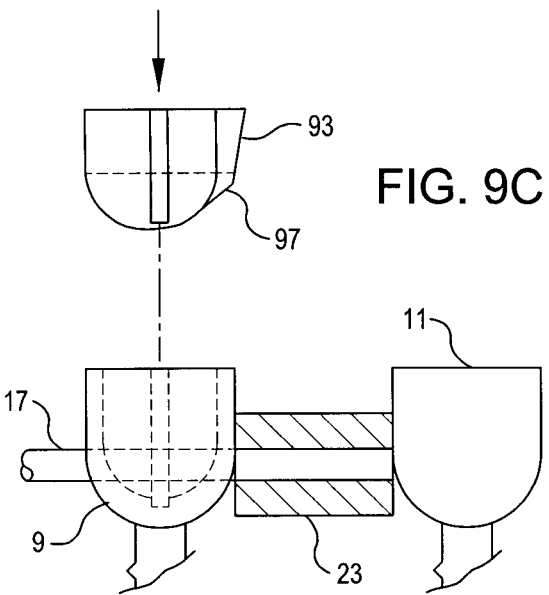
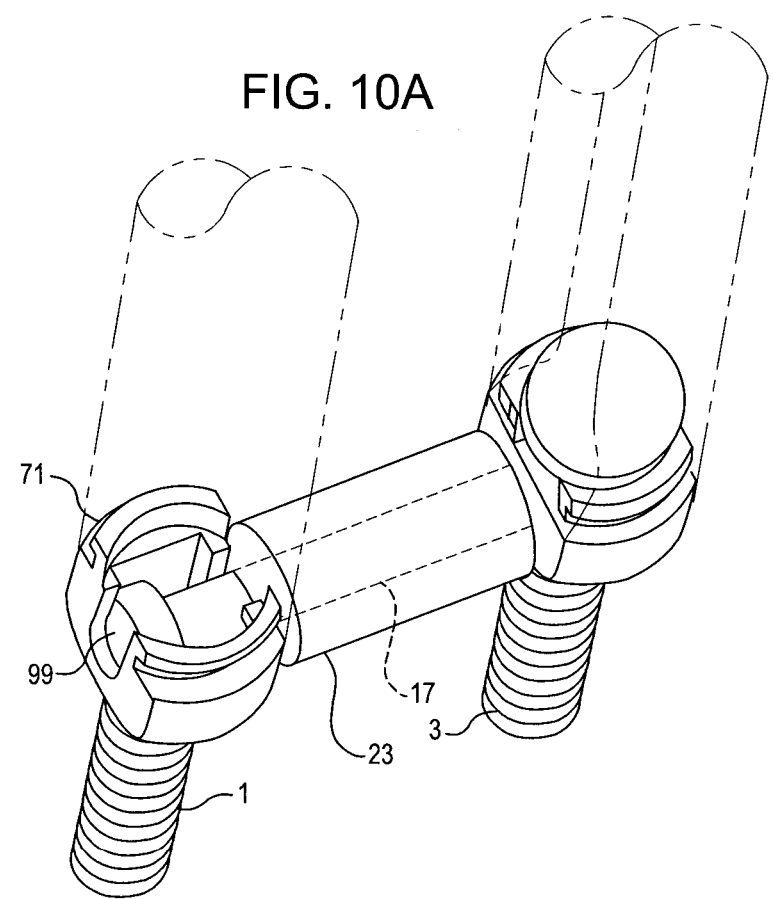

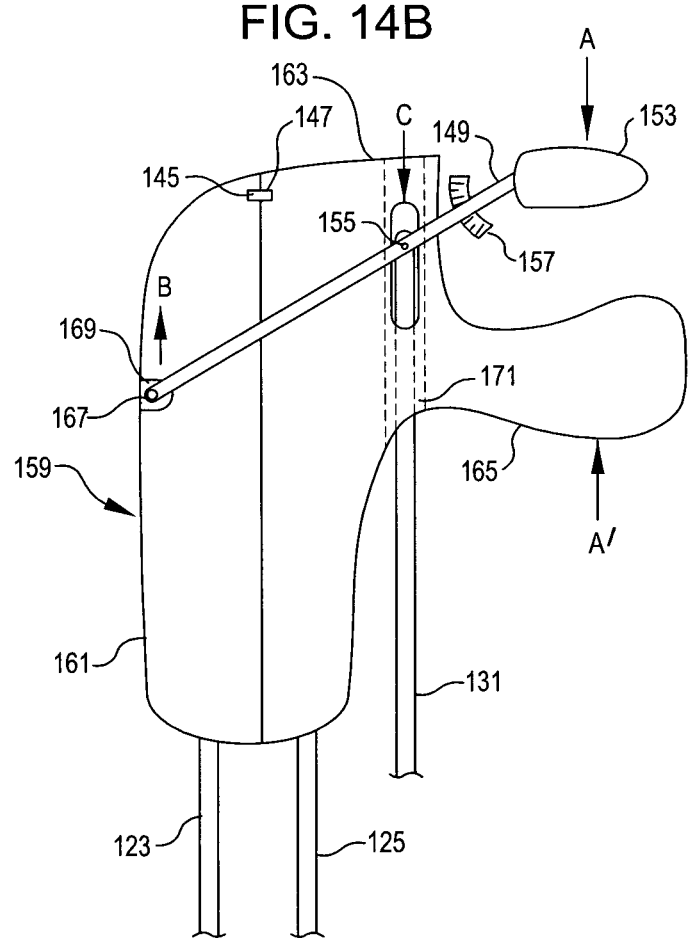

PERCUTANEOUS SYSTEM FOR DYNAMIC SPINAL STABILIZATION

CROSS-REFERENCE TO RELATED APPLICATIONS

This application claims priority to U.S. provisional patent application No. 60/823,246, filed Aug. 22, 2006.

FIELD OF THE INVENTION

The present invention relates generally to methods and systems for the treatment of disorders of the spine, and more specifically to methods and systems for dynamic stabilization of the spine.

BACKGROUND OF THE INVENTION

Lower back pain is one of the most common, and one of the most expensive, disorders afflicting industrialized societies. Conservative treatments include rest, application of ice or heat, exercise, physical therapy, narcotics, steroids and weight control. If these treatments are insufficient to control pain and allow return to normal activity, surgical treatment may be required in which all or part of one or more degenerated, ruptured or otherwise failing discs is removed. This is followed by insertion of an interbody device, for example an artificial disc or fusion implant, and/or fusion of adjacent vertebrae. While fusion surgery is effective in a majority of cases, it has several disadvantages including a reduced range of spinal motion and an increased load transfer to adjacent levels of the spine, which accelerates degeneration at those levels and increases the likelihood of later problems with adjacent spinal segments. External stabilization of spinal segments, either alone or in combination with lumbar fusion and/or implantation of interbody devices, provides significant advantages over lumbar fusion alone, including prevention or reduction of pain.

U.S. Pat. No. 6,530,929 describes instruments for use in placing a brace, or stabilization device, in for example the spine. The brace comprises at least two anchors, such as pedicle screws, that are placed in adjacent vertebrae and a generally rigid rod that extends between, and is held in place by, the two pedicle screws. This spinal stabilization system, known as the Sextant™ system, is commercially available from Medtronic, Inc. (Minneapolis, Minn.). The Sextant™ system, which employs multiaxial pedicle screw implants and pre-contoured rods that are inserted percutaneously, requires the surgeon to make three, relatively small, incisions in order to place two pedicle screws and the rod—one to insert each of the screws and one to insert the rod.

A similar system, known as the Viper™ System, is available from DePuySpine, Inc. (Raynham, Mass.). While the Viper™ system also employs pedicle screws and a generally rigid rod, it only requires the surgeon to make two incisions—one to insert each screw. This is achieved by introducing the rod through a closed screw extension using a rod holder that is rotated through 90°. While systems such as the Viper™ and the Sextant™ systems can be employed to stabilize the spine, they have the disadvantage of preventing any motion between the two adjacent vertebrae.

In order to overcome this problem, dynamic stabilization systems have been designed that are intended to stabilize the spine by controlling abnormal spinal motion while preserving near normal spine function. US published patent application no. US 2005/0143737 describes a stabilization system that employs at least one flexible element interposed between a bone anchor, such as a pedicle screw, and a generally rigid stabilization member, such as a rod or plate. Such a system, which would be difficult to implement in practice, is not yet commercially available.

The Dynesys™ system from Zimmer, Inc. (Warsaw, Ind.) is a dynamic stabilization system that is designed to bring lumbar vertebrae back into a more natural anatomical position while stabilizing affected spinal segments. This system, which is described for example in U.S. Pat. No. 7,073,415 and European Patent EP0669109B1, the disclosures of which are hereby incorporated by reference, is designed to be used either as a stand-alone treatment or in conjunction with fusion surgery. The system includes at least two pedicle screws that are anchored in adjacent vertebrae, and a flexible stabilizing cord that is threaded through, and extends between, the pedicle screws. The stabilizing cord consists of functional, working and inserting zones having varying thickness and flexibility. A separating cushion, or spacer, through which the cord passes, is positioned between the two pedicle screws. The stabilizing cord limits bending movements while the spacer holds the spinal segments in an anatomically functional position.

The Dynesys™ system is implanted by exposing the back of the spinal segment, inserting the pedicle screws into the vertebrae, cutting the spacers to the correct size, and putting the stabilizing cord in place. When employed to stabilize more than one spinal segment, the spacers are inserted segment by segment. The stabilizing cord is fixed in the eyes of the pedicle screws by mean of set screws. The surgeon can pretension the stabilizing cord separately for each spinal segment before fixing the cord in the pedicle screws, using a specially designed instrument. The stabilizing cord is then cut to the required length and the wound is closed. The main disadvantage of the Dynesys™ system is that significant spinal exposure and paraspinous muscle stripping is necessary in order to place the hardware, requiring the surgeon to make a relatively large incision. This leads to increased trauma with an associated increase in recovery time and risk of complications. In addition, the instrumentation for the Dynesys™ system is clumsy and does not permit a percutaneous approach.

US published patent application no. US 2005/0065516 discloses a spinal fixation device comprising two securing members, such as pedicle screws, and a flexible metal connection unit connected to the two securing members, wherein the metal connection unit comprises a metal tube or pipe. In certain embodiments, the outer surface of the metal tube is provided with spiral cuts or grooves to provide a desired level of flexibility.

There remains a need for an effective dynamic spinal stabilization system that can be implanted in a patient using minimally invasive procedures.

SUMMARY OF THE INVENTION

The present invention provides a minimally invasive, percutaneous system that allows for dynamic stabilization of the spine, together with methods of using the system. The system and methods disclosed herein may be effectively employed in the treatment of acute and chronic instabilities or deformities of the vertebral spine, including the thoracic, lumbar, sacral and/or cervical spine, such as, but not limited to, degenerative disc diseases, spinal stenosis, spondylolithesis, spinal deformities (for example, degenerative scoliosis, kyphosis and/or lodosis), fractures and dislocations due to physical trauma, pseudarthrosis and tumor resection. The system and methods can be used in addition to, or in place of, fusion treatment in which a surgeon removes portions of the affected disc and bone from the spine.

The disclosed minimally invasive system allows a surgeon to effectively stabilize two or more adjacent vertebrae, while maintaining some degree of motion, without making large incisions. This reduces the amount of trauma to the patient and decreases the recovery time. Using the system disclosed herein, the surgeon need only make a small number of small incisions, for example two, on each side of the spine, to give a total of four incisions, when stabilizing two adjacent vertebrae. Furthermore, each incision need only be a stab incision of about 7-10 mm in length.

In one aspect, a system is provided that comprises a first bone anchoring member, such as a pedicle screw, that is anchored in a first vertebra, and a second bone anchoring member that is anchored in a second, adjacent, vertebra. The first and second bone anchoring members, or pedicle screws, include a first head portion and second head portion, respectively, that are sized and shaped to hold a flexible elongated member, or cord. In certain embodiments, the cord is provided with a stiffened, relatively inflexible, end portion that is fixedly attached to the cord and that facilitates threading, or passing, of the cord through the first and second head portions. Preferably, the end portion of the cord is tapered. In one embodiment, the cord and/or its end portion is hollow, or cannulated, and the tip of the cord and/or end portion is open to permit threading of the cord onto a guidewire to aid in placement of the cord. The tip of the cord and/or the stiffened end portion may also, or alternatively, be provided with a protrusion that can be engaged by an instrument, such as a forceps-like instrument, thereby allowing the cord to be pulled through the first and second head portions. As detailed below, the cord and/or its end portion may be provided with an articulating joint that provides some flexibility to the cord in proximity to its tip. The system further comprises a hollow, generally cylindrical, flexible spacer that can be threaded onto the cord, and that is sized to fit between, and abut, the first and second head portions once the pedicle screws are anchored in the vertebrae.

In certain embodiments, first head portion of the first pedicle screw is provided with an aperture that extends through the head portion and is sized to receive a portion of the cord. The diameter of this aperture is smaller than the outer diameter of the spacer such that the spacer is unable to enter the aperture and instead abuts the outer face of the first head portion. Once the cord is positioned in the aperture, it is fixed in position by means of a first locking member, such as a set screw which is able to engage a threaded portion provided on the inside of a hole, or aperture, in the top of the first head portion. In one embodiment, second head portion of second pedicle screw is also provided with an aperture that extends through the head portion. The diameter of this aperture is greater than the outer circumference of the spacer, such that the spacer is able to pass through this aperture. The cord may be fixed in position in the second head portion in the same, or a similar, manner as in the first head portion.

Using this embodiment, the surgeon first anchors first and second pedicle screws in adjacent vertebrae and determines the distance between the two screws, thereby determining the required length of the spacer. The stiffened end portion of the cord is then threaded, or passed, through the apertures in the first and second head portions as detailed below, such that the cord spans the distance between the first and second head portions. The spacer is threaded onto the opposite end of the cord and pushed through the aperture in the second head portion on second pedicle screw until it abuts the first head portion of the first pedicle screw. As described below, an insert may be optionally used to prevent movement of the spacer in a reverse direction on the cord and to aid in securing the cord in the second head portion. Once the cord is secured in the first and second head portions, it is cut to the desired length.

In a second embodiment, the second head portion on the second pedicle screw is generally tulip-shaped and is provided with a generally U-shaped slot, or recess, that extends through the second head portion and that is sized to receive the cord. The cord may be fixedly held in the passageway by means of a second locking member, as described in detail below. Using this embodiment, the stiffened end portion of the cord is threaded through the aperture in the first head portion on the first pedicle screw. The spacer is then threaded along the cord until a first end of the spacer abuts the outer surface of the first head portion and a region of the cord immediately outside the second end of the spacer is placed in the slot on the second head portion and fixed in place using the second locking member.

In a related embodiment, the second pedicle screw head portion includes first and second rotatable members positioned in the U-shaped recess having first and second generally vertical faces, respectively, wherein the first and second faces are spaced apart to form a passageway for receiving the spacer mounted on a portion of the cord. Once the cord and spacer are positioned in the passageway, distal ends of the first and second faces are rotated proximally towards each other whereby the spacer is pushed along the cord and out of the head portion towards the first pedicle screw head portion.

In another aspect, a tool for grasping and retaining a portion of a flexible elongated spinal stabilization member, such as a cord, during implantation in a patient's body in provided. In one embodiment, the tool comprises a first generally U-shaped elongated member and a second generally U-shaped elongated member, wherein the outer radius of the second elongated member is smaller than the inner radius of the first elongated member. The inner surface of the first elongated member is provided with at least one first engagement member that slidably engages at least one second engagement member provided on an outer surface of the second elongated member. Following positioning of a portion of the spinal stabilization member in a lower portion of the first elongated member, second elongated member is advanced in first elongated member in a generally downwards direction with the first engagement member engaging the second engagement member, whereby distal ends of the first and second engagement members are brought into proximity with each other and grasp the spinal stabilization member.

In certain embodiments, the first engagement member is provided as an inward protrusion that extends along, but not parallel to, a longitudinal axis of the first elongated member whereby the first engagement member is closer to an outer edge of first elongated member in an upper region of the first elongated member than in a lower region of the first elongated member. The second engagement member is provided as an outward protrusion that extends along, but not parallel to, a longitudinal axis of the second elongated member whereby the second engagement member is closer to an outer edge of first elongated member in a lower region of the second elongated member than in an upper region of the second elongated member. The inner surface of the first elongated member may be provided with two opposing first engagement members and the outer surface of the second elongated member is provided with two opposing second engagement members.

In a related aspect, a tool set for applying tension to a flexible elongated spinal stabilization member during implantation in a patient is provided, the tool set comprising an elongated guide tube having an open upper end and an open lower end, the tube being sized to fit over at least a head portion of a bone anchoring member, and a retaining member that is positionable in the guide tube to grasp and retain a proximal region of the spinal stabilization member following positioning of a distal region of the spinal stabilization member in the bone anchoring member. The retaining member includes a first generally U-shaped elongated member and a second generally U-shaped elongated member having an outer radius that is smaller than an inner radius of the first elongated member, and a rigid elongated tensioning member that is positionable in the guide tube to engage, and apply tension to, a region of the spinal stabilization member. The inner surface of the first elongated member is provided with at least one first engagement member that slidably engages at least one second engagement member provided on an outer surface of the second elongated member. Following positioning of the proximal region of the spinal stabilization member in at least a portion of the first elongated member, second elongated member may be advanced in first elongated member with the first engagement member engaging the second engagement member, whereby distal ends of the first and second engagement members are brought into proximity with each other thereby grasping the proximal region of the spinal stabilization member. In certain embodiments, the tensioning member is in the form of a rod having an enlarged distal region.

The tool set may also include a handle that can be grasped by the hand of a user and that comprises a first handle member attached to the first elongated member that is able to engage a second handle member attached to the second elongated member. First and second indicators may be provided on the first and second handle members, respectively, wherein correct positioning of the first and second elongated members is indicated by mating of the first and second indicators. The tensioning member may also be movably connected to the handle.

These and additional features of the present invention and the manner of obtaining them will become apparent, and the invention will be best understood, by reference to the following more detailed description and the accompanying drawings.

BRIEF DESCRIPTION OF THE DRAWINGS

The present invention will be described in greater detail in the following detailed description, with reference to the accompanying drawings, wherein:

FIGS. 5A-5I illustrate various embodiments of a stiffened end portion provided on the cord.

FIGS. 9A-C show an embodiment of a head portion of a pedicle screw with a removable wedge for use in the dynamic stabilization system.

FIGS. 10A and 10B illustrate a cord having an enlarged region positioned in a passageway of a tulip-shaped screw head portion prior to and after, respectively, application of a locking cap.

FIGS. 11A and 11B are top views of a head portion of a pedicle screw including such rotatable elements. FIGS. 11C and D are side views of a rotatable wing element.

FIG. 12A is a side view of the tensioning system. FIG. 12B is a top view of a first elongated member and a second elongated member of the tensioning system and FIG. 12C is a perspective view of the first and second elongated members. FIGS. 12D-F, are top views of the first and second elongated members in an initial engagement position, a partially closed position and a full closed position, respectively.

DETAILED DESCRIPTION OF THE INVENTION

Figure 1:
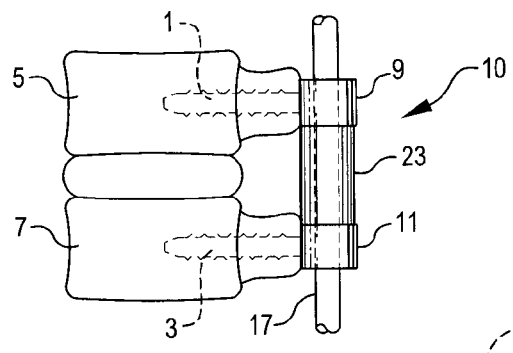
FIG. 1 is a side view of one embodiment of the dynamic stabilization system disclosed herein implanted in a spinal segment.

While in the specific embodiments described below, the system is used to stabilize two adjacent vertebrae, those of skill in the art will appreciate that the system disclosed herein may also be employed to effectively stabilize three or more adjacent vertebrae by employing additional pedicle screws and spacers. As shown in FIG. 1, in one embodiment spinal stabilization system 10 comprises two anchoring members, such as pedicle screws 1 and 3, which are anchored into adjacent vertebrae 5 and 7, respectively. Pedicle screws 1 and 3 are formed of a durable, generally rigid, biocompatible material, such as, but not limited to, carbon fiber, titanium, titanium alloys, Nitinol™, cobalt-chromium alloys and cobalt-chromium-molybdenum alloys, and may be cannulated in order to allow use of a guidewire for positioning the screws. Screws of various lengths, diameters, and threadforms may be employed, depending upon the size of the vertebrae. For example, screws 1 and 3 may have diameters of 5.5, 6.5 and 7.5 mm, and lengths from 35 to 55 mm. Each pedicle screw comprises a bone engagement portion 2 and 4, and a head portion 9 and 11. In the embodiments illustrated herein, bone engagement portions 2 and 4 are threaded. However, those of skill in the art will appreciate that other designs of bone engagement portions may be effectively employed in the systems disclosed herein. Head portions 9 and 11, which are described in detail below, each have an aperture 13 and 15 through which an elongated flexible member, or cord, 17 is passed.

Cord 17 is constructed of a flexible, durable, biocompatible material, such as, but not limited to, polyethylene terephthalate (PET). Alternatively, cord 17 may be constructed of a stiffer polymer that can be extruded or molded. In certain embodiments, cord 17 is constructed of a material whose tension varies with temperature, such that the cord tension decreases or increases as cord 17 warms from room to body temperature. Suitable materials are well known to those of skill in the art. In other embodiments, cord 17 may be in the form of a braided metal cord or wire, formed for example, by braiding filaments of stainless steel, an aluminum-nickel alloy, titanium, a titanium alloy cobalt chrome steel or other metals known to be appropriate for use in the body. If desired, cord 17 can be pre-tensioned prior to being threaded through apertures 13 and 15 using techniques and instruments well known in the art, such as those described in U.S. Pat. No. 6,616,667. The structure of cord 17 is described in detail below.

Figure 2:
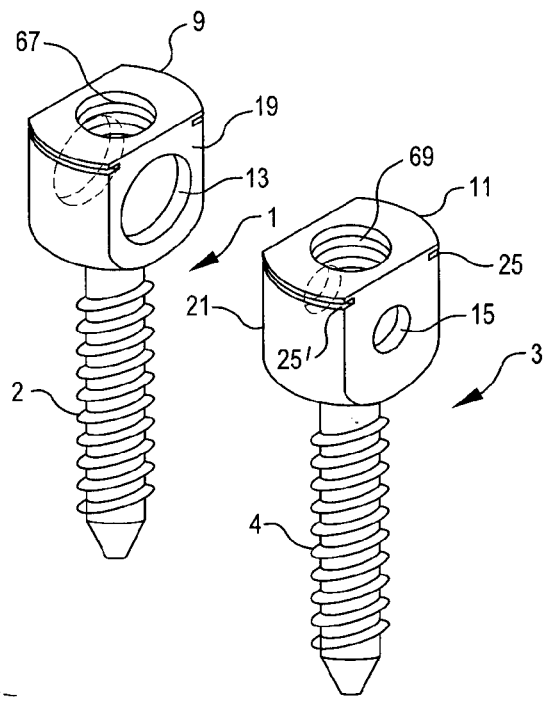
FIG. 2 shows first and second pedicle screws for use in the disclosed dynamic stabilization system.

In certain embodiments, pedicle screws 1 and 3 are polyaxial screws, whereby head portions 9 and 11 have a range of motion along several different axes, thus allowing the surgeon some flexibility in placing pedicle screws 1 and 3. As shown in FIG. 2, each of the head portions 9 and 11 is provided with two generally planar opposing sides or end faces 19 and 21 which form support surfaces for a generally cylindrical spacer 23. Spacer 23 has a tubular hollow configuration and is constructed of a durable, biocompatible material such as, but not limited to, polycarbonate urethane. In certain embodiments, spacer 23 may be formed of a material whose stiffness increases as its temperature increases following positioning in the body. Spacer 23 is positioned between pedicle screws 1 and 3, with cord 17 extending through spacer 23 along a linear axis. In embodiments where at least three pedicle screws and at least two spacers are employed per ipsilateral side, for example in systems spanning three adjacent vertebrae, spacers of different stiffness may be employed. For example, a relatively flexible spacer may be employed between a first pedicle screw positioned in a first vertebra and a second pedicle screw positioned in a second vertebra, and a relatively inflexible spacer may be employed between the second pedicle screw and a third pedicle screw positioned in a third vertebra. This is particularly useful when the second and third vertebrae are fused together. The relatively flexible spacer may be sufficiently flexible to permit a range of motion that is considered by one of skill in the art to be normal for a healthy subject, while the relatively inflexible spacer may have a flexibility that restricts movement between two adjacent bones to a level that is sufficient to permit fusion of the bones. In certain embodiments, the relatively flexible spacer is designed to allow a desired amount of movement between the adjacent vertebrae such as, but not limited to, movement of between 5 micron to 20 micron, while the relatively inflexible spacer is designed to reduce movement between adjacent vertebrae to a level sufficient to achieve fusion of the vertebrae.

As will be appreciated by those skilled in the art, pedicle screws 1 and 3, cord 17, spacer 23 and/or regions thereof may be radiopaque or may be provided with one or more radiopaque markers, in order to facilitate positioning of the system by a surgeon. Cord 17 and spacer 23 may include two different radiopaque materials in order to allow the surgeon to differentiate between the positions of these two elements.

As shown in FIG. 2, the diameter of aperture 13 in pedicle screw 1 is larger than the diameter of aperture 15 in pedicle screw. More specifically, the diameter of aperture 13 is larger than the outer diameter of spacer, while the diameter of aperture 15 is smaller than the outer diameter of spacer 23. Accordingly, spacer 23 is able to pass through aperture 13 but is unable to pass through aperture 15. Each of head portions 9 and 11 may be provided with notches or indentations 25 and 25' for engagement with guide tubes described in detail below. Other known attachment mechanisms, including, but not limited to, threads may alternatively be employed to engage head portions 9 and 11 with guide tubes.

During implantation of spinal stabilization system 10, pedicle screws 1 and 3 are anchored in adjacent vertebrae 5 and 7 using techniques well known to those of skill in the art. Head portions 9 and 11 of screws 1 and 3 are positioned such that apertures 13 and 15 are generally transverse to the axis of screws 1 and 3 and oppose each other. However, those of skill in the art will appreciate that, due to anatomy and methods necessary for placement, the axes of the apertures may not necessarily be coincident or collinear. The distance between pedicle screws 1 and 3 is measured in order to determine the required length of spacer 23. Techniques and instruments for measuring the distance between two inserted pedicle screws are well known in the art and include, for example, those described in U.S. Pat. No. 7,073,415.

Figure 3A:
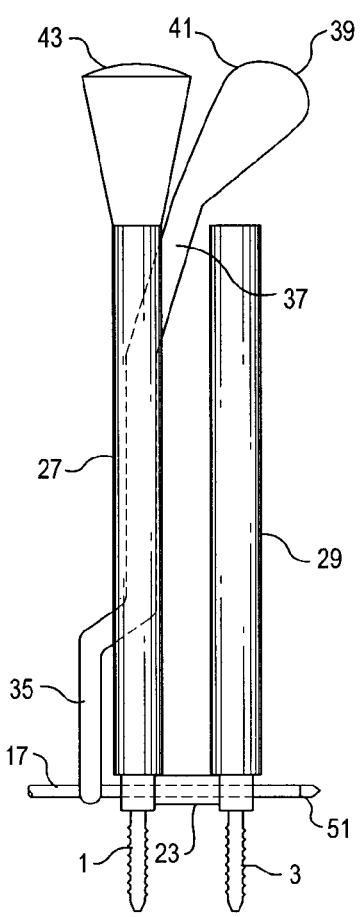
FIGS. 3A and 3B show one embodiment of the dynamic stabilization system with attached guide tubes, with FIG. 3A being a front view and FIG. 3B being a perspective view.
Figure 3B:
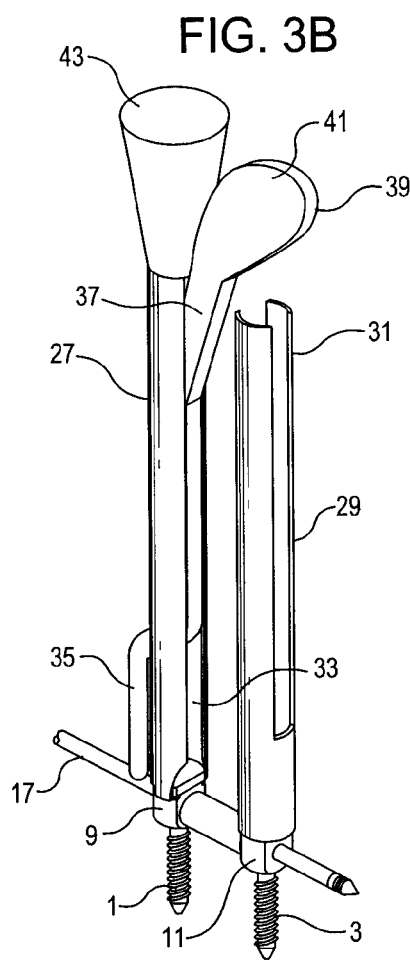

Following implantation of pedicle screws 1 and 3, closed guide tube 27 and open guide tube 29 are attached to pedicle screws 1 and 3, respectively, by means of notches 25 and 25', as illustrated in FIGS. 3A and 3B. Open guide tube 29 is provided with a generally linear slot 31 which extends along a vertical axis of extension and is open at the upper end of guide tube 29. Closed guide tube 27 is provided with a generally linear slot 33 which extends along a vertical axis of extension and is closed at the upper end of guide tube 27. Both open slot 31 and closed slot 33 are sized to receive at least a lower portion 35 and a mid-portion 37 of an elongated handle 39. At least one of open slot 31 and closed slot 33 may be provided with an enlarged opening, or cut-out 40 (shown in FIG. 10B), positioned at its lower region, for example in order to facilitate positioning of fastening screws in head portions 9 and 11 of pedicle screws 1 and 3. Upper portion 41 of handle 39 is shaped and sized to mate with a top portion 43 of closed guide tube 27. Guide tubes 27 and 29, together with handle 39, are constructed of materials currently employed in similar surgical instruments, such as surgical stainless steel. One practiced in the art will appreciate that there are other methods of providing pivots for handle 39 and for allowing handle 39 to function in a manner similar to that described above.

Figure 4A:
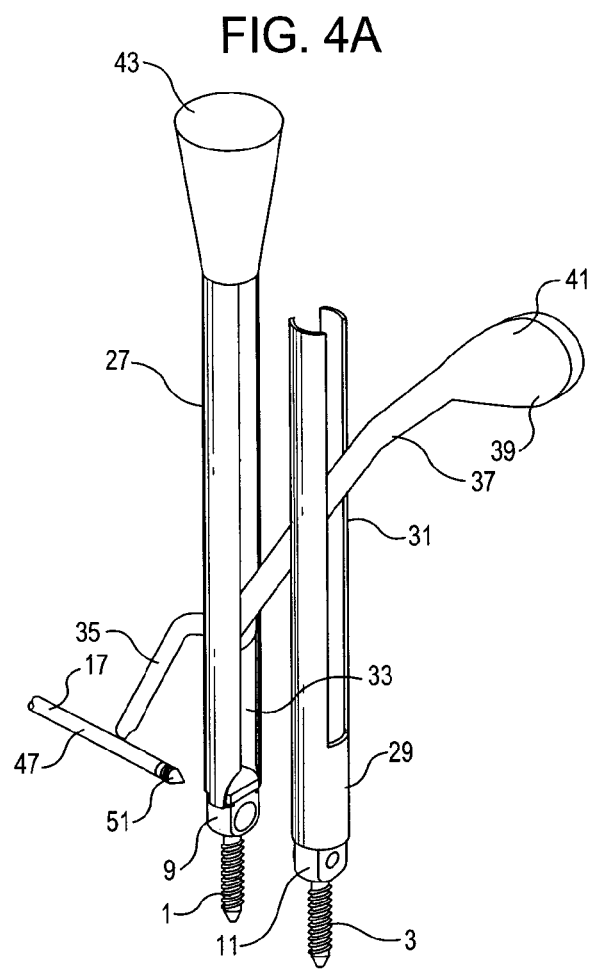
FIGS. 4A and 4B are perspective views of the embodiment of FIGS. 3A and 3B, with FIG. 4A illustrating the threading of a cord through the pedicle screws, and FIG. 4B illustrating the threading of a spacer and optional insert along the cord.

Closed guide tube 27 and open guide tube 29 are positioned such that open slot 31 and closed slot 33 are orientated in the same vertical plane. Handle 39 is then positioned in slots 31 and 33 at an angle of about 90° with respect to the vertical axis of guide tubes 27 and 29, with lower portion 35 of handle 39 extending through, and away from, closed extension 27. Tip 45 of lower portion 35 engages cord 17 at a forward, or front, region 47, for example by means of a pincer mechanism. Upper portion 41 of handle 39 is raised until it engages top portion 43 of closed guide tube. As shown in FIG. 4A, as top portion 41 is raised, handle tip 45 and cord front region 51 are directed towards pedicle screws 1 and 3, and cord 17 is threaded through apertures 13 and 15. The upper portion 41 of handle 39 is then lowered and handle tip 45 is disengaged from cord 17. An instrument, not shown, is then directed through guide tube 29 and is employed to grip, or connect with, cord front region 47 and pull it up alongside of, or alternatively into, open guide tube 29.

Figure 4B:
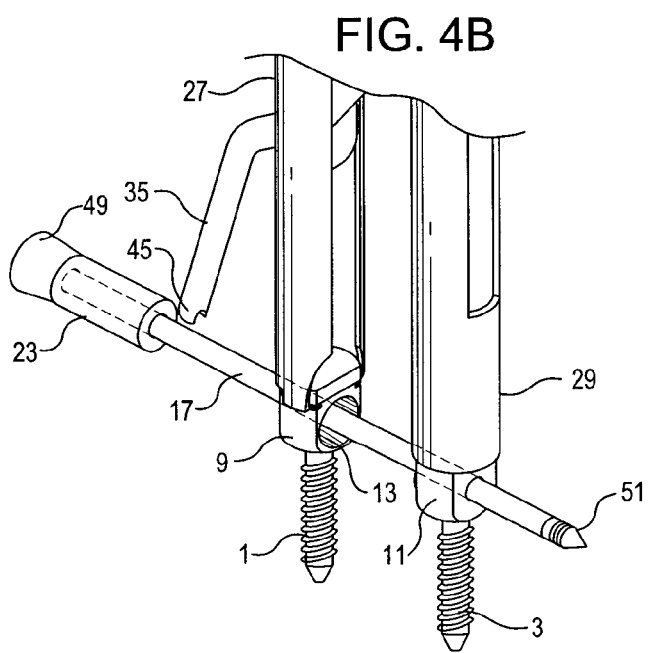

Spacer 23 and an optional insert, or locking ring, 49 are then introduced, for example through guide tube 27, threaded onto cord 17 as shown in FIG. 4B. Upper portion 41 of handle 39 is again raised, whereby handle tip 45 engages and pushes spacer 23 and optional locking ring 49 along cord 17 towards pedicle screws 1 and 3. As discussed above, spacer 23 has an outer diameter that is smaller than that of aperture 13 on pedicle screw 1 and thus passes through aperture 13 along cord 17 until it abuts end face 21 on pedicle screw 3. Locking ring 49 has an approximately circular configuration with an aperture extending through it. The diameter of this aperture is approximately the same as the inner diameter of spacer 23. However, the outer diameter of locking ring 49 is larger than the outer diameter of spacer 23 and is approximately the same as the diameter of aperture 13. Locking ring 49 thus travels along cord 17 until it enters aperture 13, and is subsequently retained in aperture 13 by application of a set screw or other fastening/locking mechanism commonly known in the art, thereby preventing any backwards movement of spacer 23. Locking ring 49 is made of a generally rigid material and may be constructed of the same material as head portion 9 of pedicle screw 1. In certain embodiments, locking ring 49 is sized to extend beyond aperture 13 along cord 17 in the direction of spacer 23, thereby exerting pressure on spacer 23.

Following positioning of spacer 23, handle 39 is removed and cord 17 is fixed in place in apertures 13 and 15 of screw head portions 9 and 11, as described below, prior to being cut at, or in proximity to, the side of head portion 9 that is distal to spacer 23.

As will be appreciated by those of skill in the art, two handles may be employed in place of handle 39. For example, a first handle may be employed to pull cord 17 through apertures 13 and 15, and a second handle may be employed to push spacer 23 and optional locking ring 49 along the cord. Alternatively, cord 17 may be pulled through apertures 13 and 15 using a forceps-like instrument, as is known in the art.

As shown in FIG. 5A, in certain embodiments, a first, distal, end of cord 17 is provided with a stiffened end piece 51 preferably constructed of a semi-rigid, biocompatible material, such as polyethylene. End piece 51 may have, but is not limited to, a length of approximately 15 to 50 mm and is fixedly attached to cord 17. End piece 51 may be generally straight or may be curved. The use of a stiffened end piece on cord 17 facilitates threading of cord 17 through apertures 13 and 15 on pedicle screws 1 and 3. End piece 51 may have a tapered tip as shown in FIG. 5A. Alternatively, as shown in FIG. 5B, end piece 51 may be provided with a protrusion 55 at its tip which can be engaged by a tool, such as a forceps- or hook-like tool, to facilitate pulling of cord 17 through apertures 13 and 15. While the protrusion illustrated in FIG. 5B has a generally doughnut-like shape, protrusions having other shapes may also be effectively employed on end piece 51. Other fastenable connections known to those skilled in the art may be employed to grasp, control and/or guide end piece 51 such that cord 17 is threaded through apertures 13 and 15, and end piece 51 is removed through, or alongside of, guide tube 29.

In yet another embodiment, both cord 17 and end piece 51 are cannulated, and end piece 51 is provided with an open tip 57 as shown in FIG. 5C. In this embodiment, a guidewire 59 may be first threaded through apertures 13 and 15 in pedicle screws 1 and 3, for example essentially as described above. Cord 17 is then threaded over guidewire 59 and through apertures 13 and 15. Alternatively, a cannulated cord 17, without a stiffened endpiece, may be employed in conjunction with a guidewire. In this embodiment, the cord is preferably formed of a comparatively stiff material. Distal end piece 51 may include a joint which may be partially opened in order to allow some flexibility. An example of such a joint is shown in FIG. 5D. In this embodiment, end piece 51 includes a first portion 61 provided with a first locking mechanism 63 which mates with a second locking mechanism (not shown) located on the inside of a second portion 65 of end piece 51, wherein the first and second portions can pivot with respect to each other. When first portion 61 is pushed towards second portion 63, the two locking mechanisms engage thereby locking portions 61 and 63 together. When first portion 61 and second portion 63 are pulled away from each other, the two locking mechanisms partially, but not completely, disengage, thereby allowing end piece 51 to flex. In this embodiment, second portion 63 is first pushed through and then pulled if necessary.

In an alternate embodiment, illustrated in FIGS. 5E-T, first and second portions 61 and 65 are provided with a mechanism such that, when first portion 61 is pushed and second portion 65 experiences some resistance to that pushing, the first and second portions become slidably engaged, for example by means of fingers 62 and 62' protruding from first portion 61 and second portion 65, respectively, towards each other. Fingers 62 and 62' interdigitate during engagement to make a single assembly. When pulled, the second portion 65 slides apart from first portion 61 disengaging the interdigitation while remaining attached via, for example, a hinge pin 64 in slots 66 and 66' or a similar mechanism. This enables second portion 65 to pivot around a corner before first portion 61 thus providing a system that can turn a sharper corner (i.e. transverse a shorter radius curve), allowing the end piece 51 to be pulled up through, or alongside, tube 29 in a smaller space and with less adjacent tissue disruption and potential damage. Other flexible member mechanisms that are employed in flexible drill shafts and similar items may also, or alternatively, be incorporated into end piece 51 in order to allow it to flex off axis while remaining fairly stiff for pushing along the major axis.

Figure 10B:
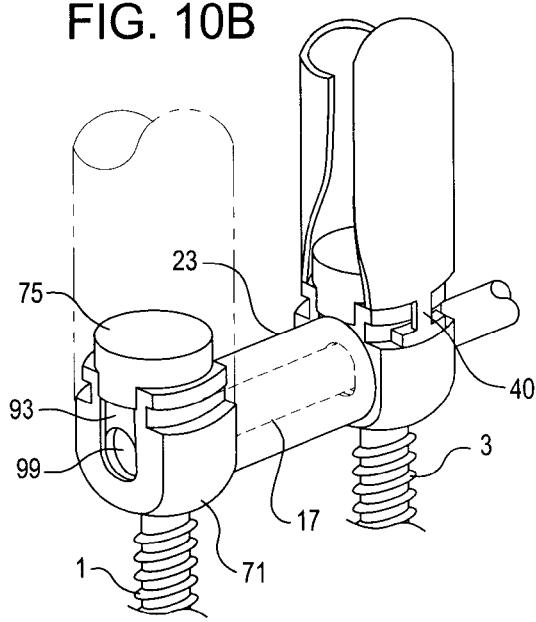

In another embodiment, cord 17 is provided with an enlarged, or substantially stiffer, region 99 at, or in proximity to, its second, proximal, end. FIGS. 10A and 10B illustrate a cord 17 having an enlarged region 99 positioned in a passageway of a tulip-shaped screw head portion 71 prior to and after, respectively, application of, for example, a locking cap 75. Enlarged region 99 may be formed of a material that can be swaged and thereby securely attached to cord 17, such as a compressible metal, polymer or ceramic. Those of skill in the art will appreciate that other techniques may be employed for attaching enlarged region 99 to cord 17. Enlarged region 99 preferably has a diameter that is greater than that of passageway 73 in the head portion, and thereby aids in retaining cord 17 in passageway 73. Following positioning of cord 17 in the head portion of pedicle screw 3 and application of a set screw, enlarged region 99 assists in retaining cord 17 in the head portion.

As illustrated in FIG. 2, head portions 9 and 11 of pedicle screws 1 and 3 are each provided with a threaded hole 67 and 69, respectively, for receiving a set screw (not shown). Once cord 17 is positioned and appropriately tensioned in apertures 13 and 15, and spacer 23 is positioned on cord 17 between pedicle screws 1 and 3, cord 17 is fixed in place by screwing the set screws into threaded holes 67 and 69 using instruments and techniques well known in the art, for example as described in U.S. Pat. No. 7,073,415, the disclosure of which is hereby incorporated by reference. Other types of clamping mechanisms may additionally, or alternatively, be employed to hold cord 17 in position in apertures 13 and 15. For example, the set screw may be provided with a penetrating element that at least partially penetrates the cord to hold it in position.

Figure 6:
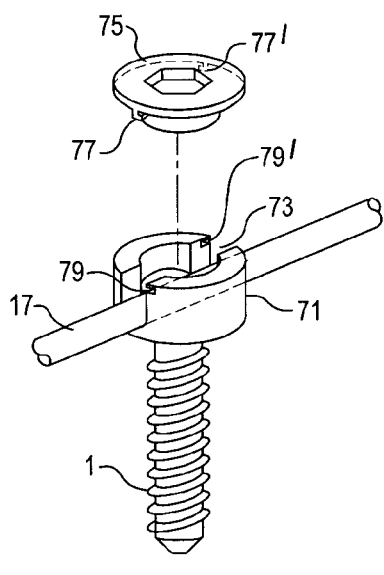
FIG. 6 shows an alternative embodiment of a pedicle screw for use in the disclosed dynamic stabilization system.

In an alternative embodiment, illustrated in FIG. 6, pedicle screw 1 is provided with an open, generally tulip-shaped, head portion 71 having a generally U-shaped passage 73 extending through it. Passage 73 is sized to receive cord 17. In this embodiment, end portion 51 of cord 17 is threaded through aperture 15 in pedicle screw 3, spacer 23 is positioned on cord 17 between pedicle screws 1 and 3, and cord 17 is placed in passage 73. Locking cap 75 is then fixedly positioned in the top of head portion 71, thereby securing cord 17 in place in passage 73. Many mechanisms known in the art may be effectively employed to fixedly hold locking cap 75 in place on head portion 71 including, but not limited to, those disclosed in U.S. Pat. No. 6,783,527, the disclosure of which is hereby incorporated by reference. For example, locking cap 75 may be provided with a threaded portion that engages a threaded portion provided on head portion 71. Alternatively, as shown in FIG. 6, locking cap 75 may be provided with two protrusions 77 and 77' positioned on opposing sides of locking cap 75 which engage notches, or slots, 79 and 79' provided on inner surfaces of passage 73. In use, locking cap 75 is positioned on head portion 71 with protrusions 77 and 77' positioned in passage 73. Locking cap 75 is then rotated through 90°, whereby protrusions 77 and 77' enter, and are retained by, notches 79 and 79'. Other types of locking caps that may be employed with the present system include, for example, the Monarch™ typhoon cap available from DePuy Spine.

Figure 7:
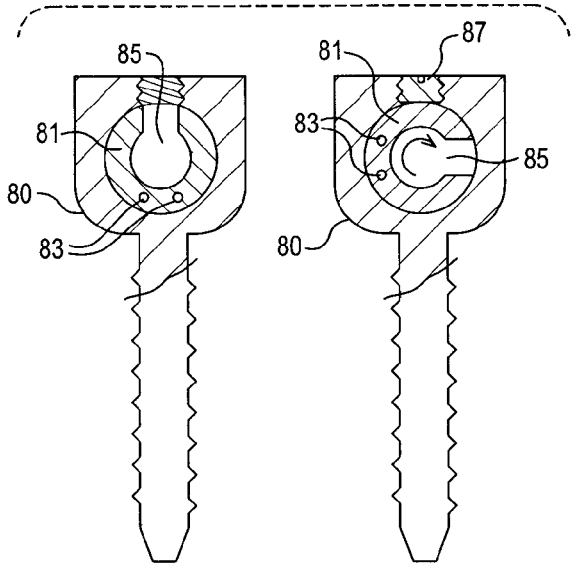
FIG. 7 shows an embodiment of a head portion of a pedicle screw with insert for use in the dynamic stabilization system.

In yet another embodiment, illustrated in FIG. 7, pedicle screw 1 includes a head portion 80 having a slotted insert 81, whose outer configuration matches the inner configuration of head portion 80 so that insert 81 is retained in head portion 80. Slotted insert 81 is provided with an open passage, or slot, 85 which is sized to receive cord 17. Once cord 17 is placed in slot 85, insert 81 is rotated by means of an instrument attached, for example, to attachments points 83, thereby trapping the cord within slot 85. Cord 17 and insert 81 may be further retained in place by set screw 87.

Figure 8A:
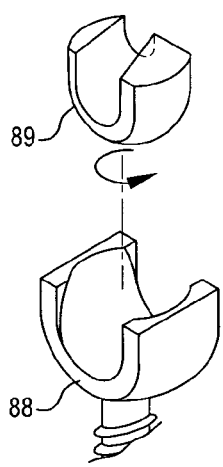
FIGS. 8A-C show an embodiment of a head portion of a pedicle screw with a rotatable inner member for use in the disclosed dynamic stabilization system.
Figure 8B:
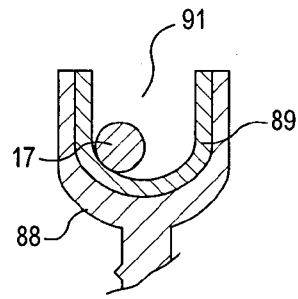
Figure 8C:
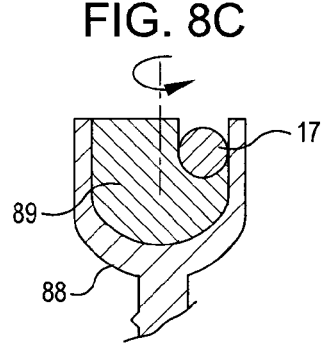

In the embodiment illustrated in FIGS. 8A-C, pedicle screws 1 and 3 are provided with a head portion 88 that comprises a rotatable inner member 89 that is sized to be received within head portion 88 and is able to rotate around an approximately vertical axis of head portion 88. Inner member 89 is provided with a passageway 91 that is sized to receive cord 17 and that may or may not be open at the top. After cord 17 is positioned in passageway 91, inner member 89 is rotated, thereby locking cord 17 in head portion 88.

Figure 9A:
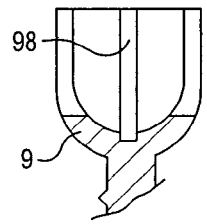
Figure 9B:
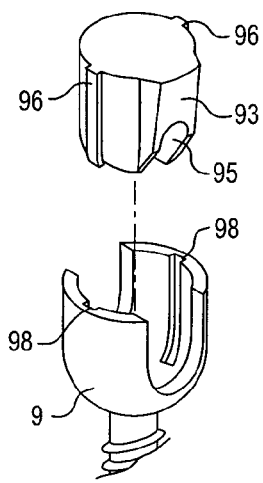

In the embodiment illustrated in FIGS. 9A-C, a wedge 93 is employed in place of a locking ring 49 in an open head portion 9 of pedicle screw 1. Wedge 93 includes a groove 95 that is sized to receive cord 17, and that may be tapered at a lower edge 97 in one or two dimensions. In addition, wedge 93 is provided with two protrusions 96 positioned on opposing sides of the wedge that mate with and can be retained in grooves 98 provided on opposing sides of the inner surface of hear portion 9. Once cord 17 is positioned in head portion 9, wedge 93 is pushed down into head portion 9, thereby applying force to spacer 23 and pushing it towards head portion 11 in order to tighten spacer 23 into position.

Figure 11A:
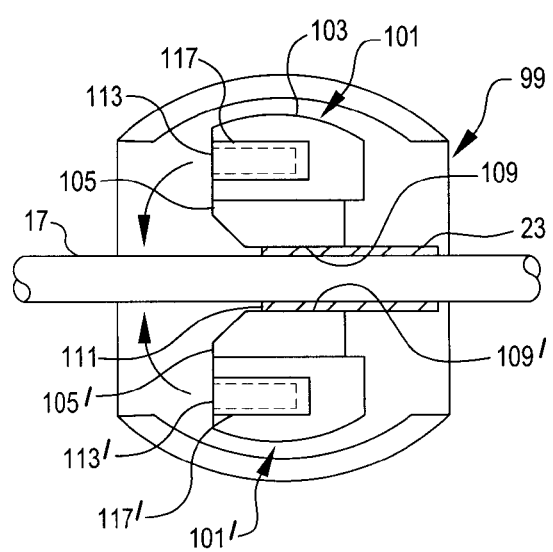
FIGS. 11A-D illustrate the use of rotatable wing elements in the head portion of a pedicle screw for placing and retaining a spacer on a cord.
Figure 11B:
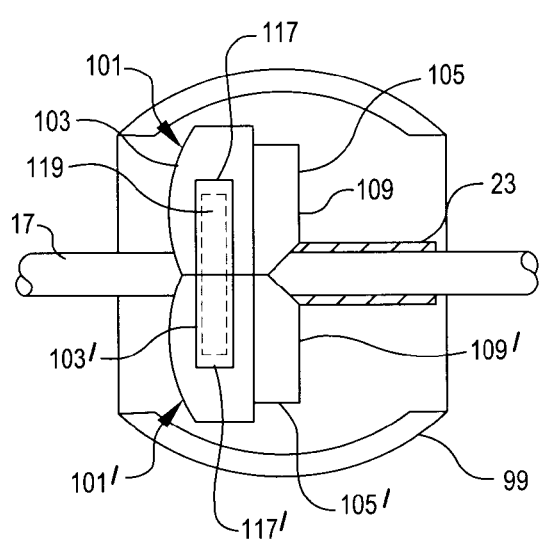
Figure 11C:
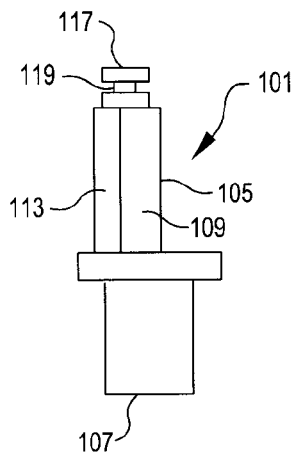
Figure 11D:
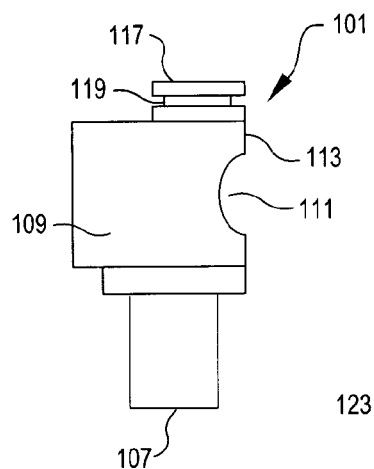

In yet a further embodiment, illustrated in FIGS. 11A-D, at least one of pedicle screws 1 and 3 is provided with a tulip-shaped head portion 99 that contains two opposing rotatable wing elements 101 and 101'. Each element 101 and 101' comprises an upper locking portion 103 and 103', an engagement portion 105 and 105' and a lower, generally cylindrical, portion 107 and 107'. Cylindrical portions 107 and 107' are rotatably held in at least one aperture in head portion 99 (not shown) and can be rotated in the aperture(s) by, for example, a gearing or other drive mechanism. In an initial, open, position (shown in FIG. 11A), wing elements 101 and 101' are in a spaced-apart configuration such that first generally vertical faces 109 and 109' on elements 101 and 101', respectively, oppose each other and form a passageway 111 that is sufficiently large to accommodate cord 17 with spacer 23 threaded onto the cord. Once spacer 23 is positioned between faces 109 and 109', wing elements 101 and 101' are rotated in a generally horizontal (relative to the longitudinal axis of the screw) plane towards each other using, for example, an instrument attached to an upper region of wing elements 101 and 101', such that second generally vertical faces 113 and 113' on wing elements 101 and 101', respectively, are brought together or into proximity with each other. Spacer 23 is thus pushed along cord 17 and out of head portion 99, as shown in FIG. 11B. As shown in FIGS. 11C and D, second faces 113 and 113' are each provided with a generally horizontal elongated cut-out, or depression, 115 and 115', which are sized to receive cord 23 when wing elements 101 and 101' are in a closed position. Similarly, first faces 109 and 109' may be provided with generally horizontal elongated cut-outs or depressions sized to receive spacer 23.

Once wing elements 101 and 101' are in a closed position, a locking mechanism is applied to prevent movement of the wing elements. For example, a locking bar (not shown) may be positioned on the upper surface of, and extend between, rotatable wing elements 101 and 101'. Alternatively, upper surfaces of wing elements 101 and 101' may each be provided with an upward protrusion 117 and 117'. As shown in FIGS. 11C and D, in one embodiment, protrusions 117 and 117' include an undercut, or groove 119 for receiving and retaining a locking wire, or loop. The locking wire is sized to fit over protrusions 117 and 117' and may be crimped into groove 119, thereby locking wing elements 101 and 101' in a closed position. Alternatively, protrusions 117 and 117' may be provided with apertures extending through them that are sized to receive and retain a locking pin. Once wing elements 101 and 101' are in a closed position, the locking pin is inserted through the apertures in protrusions 117 and 117' thereby securing wing elements 101 and 101' in position. Those of skill in the art will appreciate that other mechanisms may be employed to hold wing elements 101 and 101' in a closed, or locked, position.

Figure 12B:
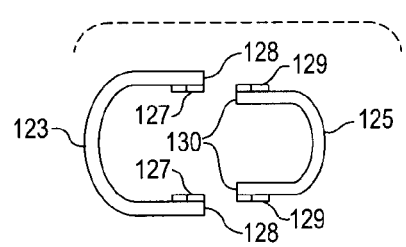
FIGS. 12A-F illustrate a tensioning system that may be employed to tension a cord extending between at least two pedicle screws.
Figure 12A:
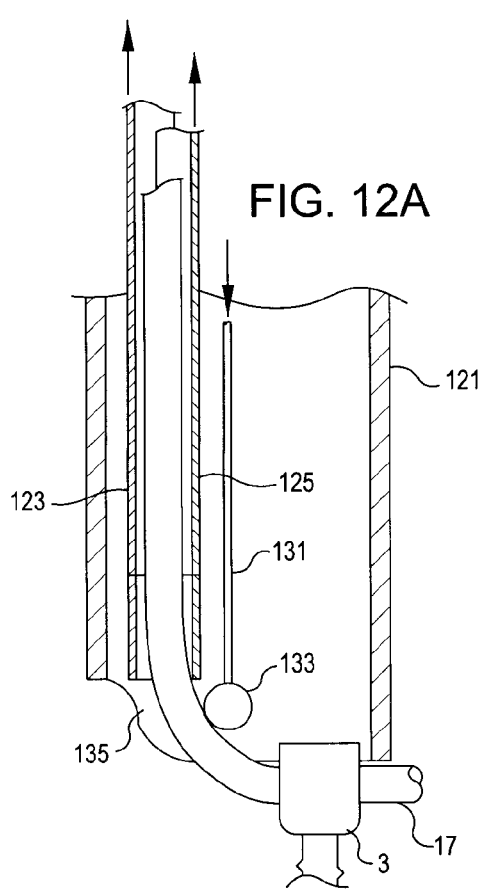
Figure 12C:
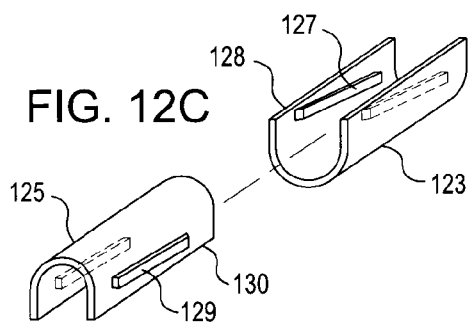

FIG. 12A illustrates a tensioner that can be employed to tension a cord once cord 17 has been locked in place in a first pedicle screw (not shown) and positioned in a head portion 99 of a second pedicle screw 3. An elongated working, or guide, tube 121 is sized to fit over pedicle screw head portion 99. A first elongated member 123 and a second elongated member 125 are positioned in a generally vertical orientation within working tube 121. As shown in FIG. 12B, both first elongated member 123 and second elongated member 125 have a generally semi-circular cross-section. First elongated member 123 has a larger radius than second elongated member 125 and is provided with opposing inwardly-extending protrusions 127 on its inner surface that extend along, but are not parallel to, the longitudinal axis of member 123. Rather, as shown in FIG. 12C, protrusions 127 are angled such that they are closer to outer edges 128 of elongated member 123 in the upper region of member 123 than in the lower region of member 123. Second elongated member 125 is provided with outwardly-extending protrusions 129 on its outer surface extending along the longitudinal axis of member 125 and is sized to be received within first elongated member 123, such that protrusions 129 slidably engage protrusions 127. Protrusions 129 are angled such that they are closer to outer edges 130 of member 125 in the lower region of member 125 than in the upper region. The inner surface of second elongated member 125 is sized to receive cord 17. The inner surfaces of first and second elongated members 123 and 125 may be provided with ridges, knurls and/or other protrusions in order to enhance their ability to grasp and securely retain the outer surface of cord 17. Those of skill in the art will appreciate that other mechanisms may be employed to grip cord 17, such as a mechanism similar to a pair of pliers or a parallelogram system whereby when one elongated member is moved proximally, the working end collapses onto, and thus retains, the cord.

Figure 12D:
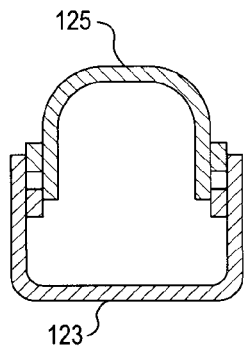
Figure 12E:
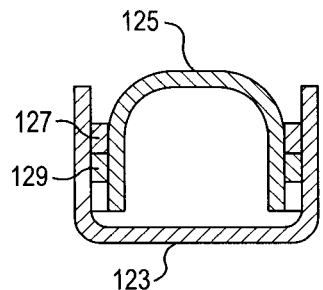
Figure 12F:
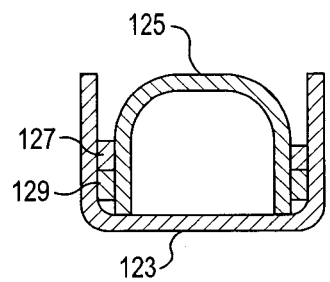

Once cord 17 is locked in the first pedicle screw (not shown) and positioned, but not locked, in head portion 99 of screw 3, which may or may not be adjacent to the first pedicle screw, the cord is securely grasped by first advancing first elongated member 123 in a downward direction until it contacts cord 17. Second elongated member 125 is then advanced in a downward direction with inwardly extending protrusions 127 slidably engaging outwardly extending protrusions 129 on first elongated member 123 as shown in FIG. 12C. As shown in FIGS. 12D-F, due to the angled positioning of protrusions 127 and 129, the lower regions of first elongated member 123 and second elongated member 125 are drawn closer together as second elongated member 125 is moved in a downward direction, whereby cord 17 is firmly grasped between, and retained by, the first and second elongated members. If desired, cord 17 may be pulled generally upwards by moving first and second elongated members 123 and 125 in an upwards direction, thereby removing any slack from the cord.

An elongated, generally rigid, tensioning member 131 having an enlarged distal region 133 is then placed in working tube 121, such that enlarged distal region 133 engages cord 17 at a location between screw 3 and first and second elongated members 123 and 125. Tensioning member 131 is then urged in a generally downward direction while first and second elongated members 123 and 125 are either held in place or urged in a generally upward direction, thereby applying tension to cord 17. Tensioning member 131 may alternatively, or additionally, be provided with a bend in its shaft at a lower region to aid in applying pressure to cord 17. Cord 17 is then locked in position in the head portion of screw 3 as discussed above. Cord 17 may be cut to the desired length using, for example, a guillotine-type cutter. As shown in FIG. 12A, working tube 121 may be provided with an aperture 135 at a lower or distal region in order to accommodate bulging of cord 17 when pressure is applied by tensioning member 131.

Figure 13A:
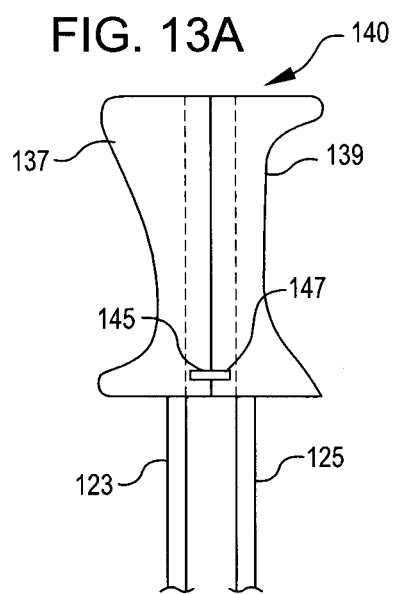
FIGS. 13A and B are side and top views, respectively, of a handle for use with the tensioning system of FIGS. 12A and B.
Figure 13B:
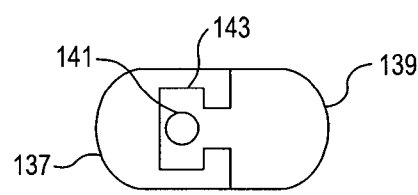

As illustrated in FIG. 13A, first and second elongated members 123 and 125 are connected at their upper, or proximal, ends to first and second handle members 137 and 139, respectively. Handle members 137 and 139 may be engaged to form a handle 140, which is shaped to be grasped by the hand of a user. First handle member 137 and second handle member 139 are matingly engaged, for example by way of an interlocking protrusion 141 on second handle member 139 which is received, and slidably held, by aperture 143 on first handle member 137, as shown in FIG. 13B, thus ensuring correct vertical alignment of first and second elongated members 123 and 125. In order to indicate when the distal ends of first and second elongated members 123 and 125 are correctly aligned, first and second handle members 137 and 139 may be provided with indicators 145 and 147 that align, and/or snap together when first and second elongated members 123 and 125 are correctly positioned. While indicators 145 and 147 are illustrated in FIG. 13A as being in a lower region of handle 140, it will be appreciated that they may alternatively be located in a mid-region or upper region of handle 140. Those of skill in the art will appreciate that other methods of indicating alignment may be employed.

Once first and second elongated members 123 and 125 are correctly aligned and locked into position with each other and cord 17 is securely grasped, an elongated, generally rigid, rod 149 is movably attached at a first end to the upper surface of handle 140 by, for example, hinge connector 151. At its second end, elongated rod 149 is provided with a handle, or knob, 153. Tensioning member 131 is rotatably attached at or near its upper end to rod 149 by means, for example, of a pin 155, at a region on rod 149 that is located between hinge connector 151 and knob 153. Movement of knob 153 in a generally downwards direction thus causes tensioning member to be pushed in a generally downwards direction while simultaneously urging first and second elongated members 123 and 125 in a generally upwards direction. A calibrated scale 157 may be provided to enable the user to determine the amount of force that is being applied to tensioning member 131. Those of skill in the art will appreciate that tensioning member 131 may alternatively be positioned in a channel provided in handle 140 as in the embodiment illustrated in FIG. 14B.

Figure 14A:
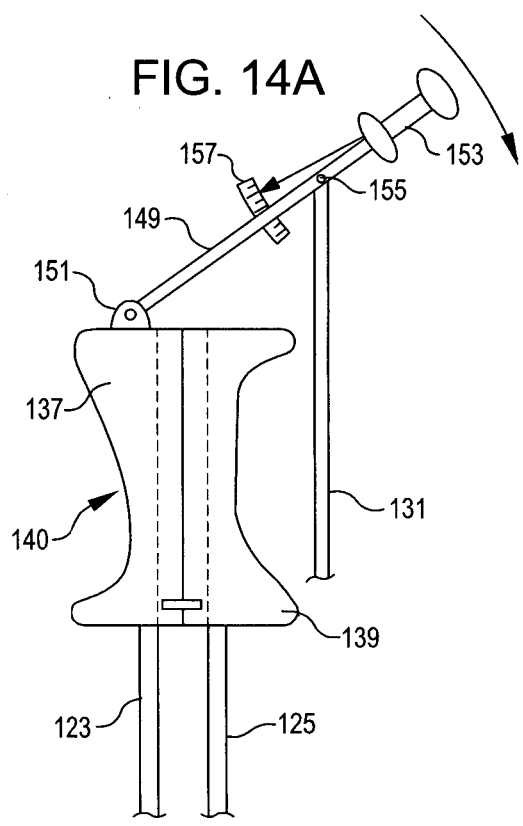
FIGS. 14A and B are side views of a first and a second embodiment, respectively, of a tensioning system disclosed herein.

FIG. 14B shows an embodiment of a tensioner handle 159 having a "pistol-grip" configuration. Handle 159 comprises a first handle member 161 and a second handle member 163, with second handle member 163 having a protrusion 165 extending from one side that is sized and shaped to be gripped by a user. Rod 149 is rotatably attached to first handle member 161 by means, for example, of a pin 167 located in an aperture 169 in a region of first handle member 161 that is positioned away from, or distal to, protrusion 165. Alternatively, rod 149 may be formed of two elongated members connected by a small, generally perpendicular section that is retained in aperture 169. Tensioning member 131 is positioned in channel 171 in second handle member 163 and, as in the embodiment of FIG. 14A, is rotatably attached to rod 149, for example by means of pin 155. In use, the surgeon grasps protrusion 165 and knob 153 and squeezes them together in the direction indicated by arrows A and A'. This causes handle 159 to be urged in a generally upwards direction as indicated by arrow B, and tensioning member 131 to be urged in a generally downwards direction as indicated by arrow C, thereby keeping handle members 161 and 163 locked together while simultaneously applying tension to cord 17 whereby pedicle screw 3 can be locked with a surgeon-determined amount of tension applied to the cord.

While the present invention has been described with reference to specific embodiments thereof, it should be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims.

All of the publications, patent applications, and patents cited in this application are herein incorporated by reference in their entirety to the same extent as if each individual publication, patent application or patent was specifically and individually indicated to be incorporated by reference in its entirety.

We claim:

1. A system for stabilizing at least two vertebrae, comprising:
   (a) a flexible, elongated member having a length sufficient to extend between a first vertebrae and a second vertebrae;
   (b) a first generally cylindrical spacer having an aperture extending along a longitudinal axis thereof, wherein the aperture is sized to receive a portion of the elongated member;
   (c) a first bone anchoring member comprising a first head portion and a first bone anchoring portion, wherein the first head portion has two first flat outer faces and a generally transverse aperture that extends between the two first flat outer faces and is sized to receive a first portion of the elongated member, the transverse aperture having a diameter that is smaller than an outer diameter of the spacer;
   (d) a second bone anchoring member comprising a second head portion and a second bone anchoring portion, wherein the second head portion is provided with an opening that extends through the second head portion in a generally transverse direction and is sized to receive a second portion of the elongated member and to allow passage of the spacer through the opening, whereby the entire spacer is capable of passing through the opening;
   (e) a first locking member for retaining the first portion of the elongated member in the first head portion; and
   (f) a second locking member for retaining the second portion of the elongated member in the second head portion,
   (g) a locking ring having a transverse aperture that is sized to receive the second portion of the elongated member, wherein a diameter of an outer surface of the locking ring is larger than that of an outer surface of the spacer, and wherein the locking ring is sized to be retained in the opening of the second head portion,
   wherein the spacer is sized to fit between the first and second head portions whereby, once the first and second portions of the elongated member are positioned in the first and second head portions, the spacer member can be threaded along the elongated member and through the second head portion until a first end of the spacer abuts one of the first flat outer faces of the first head portion and a second end of the spacer abuts a surface of the locking ring following positioning of the locking ring on the elongated member proximal to the spacer, whereby the locking ring prevents movement of the spacer in a proximal direction.

2. The system of claim 1, wherein the opening in the second head portion is in the form of a generally transverse aperture.

3. The system of claim 2, wherein the elongated member is provided with a stiffened region at, or in proximity to, its distal end.

4. The system of claim 2, wherein the elongated member is cannulated, whereby the elongated member may be threaded onto a guidewire to facilitate placement of the elongated member in the first and second head portions.

5. The system of claim 2, wherein the elongated member is provided with a protrusion at, or in proximity to, its distal end, whereby the protrusion may be grasped by an instrument and pulled through the first and second head portions.

6. The system of claim 2, wherein the elongated member is constructed of a material whose tension varies with temperature, and the tension of the elongated member decreases as the elongated member warms from room to body temperature.

7. The system of claim 2, wherein the elongated member is in the form of a braided metal cord.

8. The system of claim 2, wherein the spacer is sized to extend between the first and second head portions when the first and second bone anchoring members are positioned in the bones.

9. The system of claim 2, wherein the spacer is formed of a material whose stiffness increases as the spacer warms from room temperature to body temperature.

10. The system of claim 2, wherein at least one of the first and second bone anchoring members is a polyaxial pedicle screw.

11. The system of claim 2, wherein at least one of the first and second bone anchoring portions is cannulated.

12. The system of claim 2, wherein at least one of the first and second locking members is a set screw which is able to engage a threaded portion provided on an inner surface of a top aperture provided in a top surface of the first or second head portion.

13. The system of claim 2, further comprising:
   (a) a third bone anchoring member having a third bone anchoring portion for placement in a third vertebrae; and
   (b) a second generally cylindrical spacer sized to extend between the second and third bone anchoring members, wherein the first and second spacers have different flexibilities.

14. The system of claim 13, wherein one of the first and second spacers has a flexibility that permits movement between two adjacent vertebrae selected from the first, second and third vertebrae and the other of the first and second spacers has a flexibility that restricts movement between two different adjacent vertebrae selected from the first, second and third vertebrae to a level that is sufficient to permit fusion of the two adjacent vertebrae selected from the first, second and third vertebrae.

* * * * *